United States Patent [19]

Yamaguchi et al.

[11] Patent Number: 4,677,983

[45] Date of Patent: Jul. 7, 1987

[54] METHOD AND APPARATUS FOR MEASURING CIRCULATORY FUNCTION

[75] Inventors: Keiji Yamaguchi, Shimizu; Hideo Ishizaka, Hatano, both of Japan

[73] Assignee: Terumo Corporation, Tokyo, Japan

[21] Appl. No.: 838,604

[22] Filed: Mar. 11, 1986

[30] Foreign Application Priority Data

Mar. 11, 1985 [JP] Japan ................... 60-46379

[51] Int. Cl.4 ............................................... A61B 5/02
[52] U.S. Cl. ..................................... 128/680; 128/682; 128/689
[58] Field of Search ............... 128/677, 680, 682, 683, 128/687, 689

[56] References Cited

U.S. PATENT DOCUMENTS 4,214,589  7/1980  Sakamoto ........................ 128/680
4,475,557  10/1984  Hatschek et al. ............... 128/680 X
4,501,281  2/1985  Furukawa ........................ 128/680

FOREIGN PATENT DOCUMENTS 2621574  12/1976  Fed. Rep. of Germany ...... 128/680
2006961  5/1979  United Kingdom ............... 128/682

Primary Examiner—Lee S. Cohen
Attorney, Agent, or Firm—Staas & Halsey

[57] ABSTRACT

A method and apparatus for measuring the circulatory function of a living body in which a systolic blood pressure value is measured based on recognition of an initial Korotkoff sound made at the start of a reduction in pressure of a pressurized cuff affixed to a patient's arm. After the recognition of the initial Korotkoff sound, conditions are relaxed to enable measurement of pulse rate, judgment of the correctness of the systolic blood pressure value and a dicision as to whether applied pressure is adequate, all on the basis of sounds from the patient's blood vessel. Finally, diastolic blood pressure is measured based again on recognition of the Korotkoff sound.

24 Claims, 8 Drawing Figures

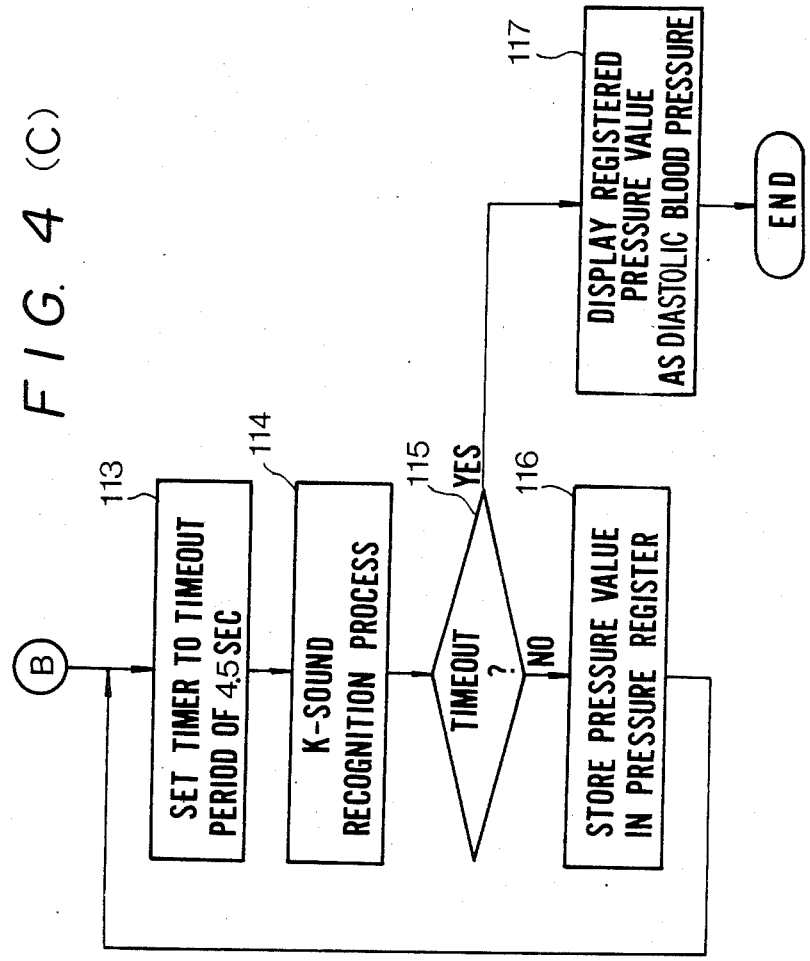

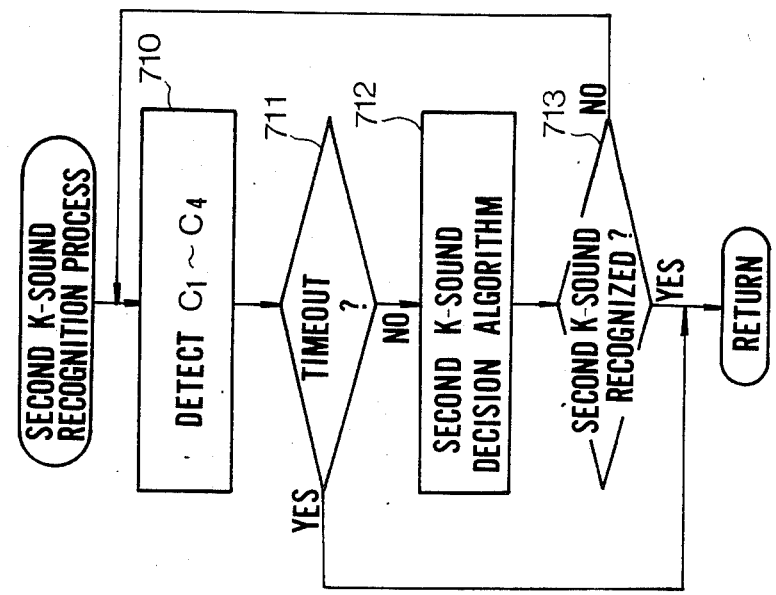
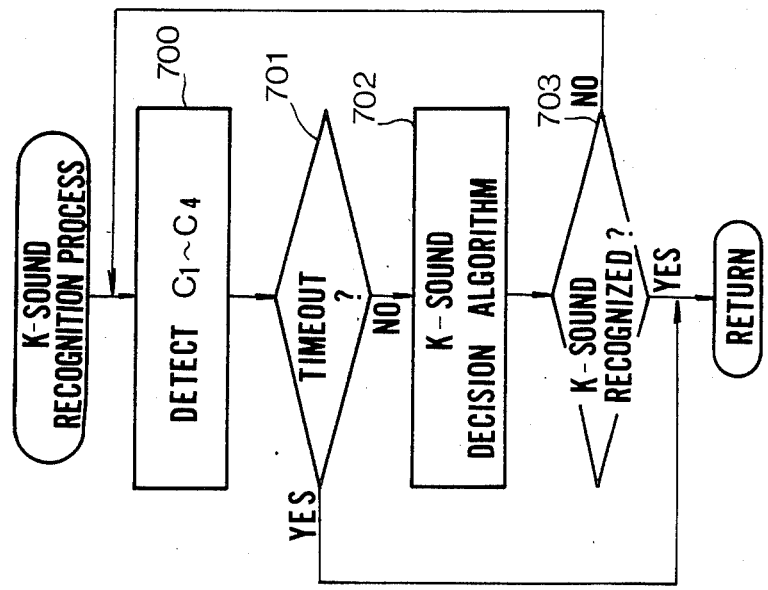

METHOD AND APPARATUS FOR MEASURING CIRCULATORY FUNCTION

BACKGROUND OF THE INVENTION

1. Field of the Invention

This invention relates to a method and apparatus for measuring the circulatory function of a living body based on the principle of auscultation, and more particularly relates to a method and apparatus for measuring the blood pressure and pulse rate of a living body.

2. Description of the Prior Art

Methods of detecting Korotkoff sounds (hereafter referred to as "K-sounds") in a blood pressure measuring apparatus which operates based on the principle of auscultation include a method employing a filter comparator, in which the K-sounds are discriminated by using a preset threshold value, and a method relying upon pattern recognition, in which the K-sounds are discriminated based on a certain pattern.

In auscultation, also referred to as stethoscopy, a stethoscopic examination of pulse is made while gradually depressurizing a pressure cuff at a rate of 2-3 mmHg per heartbeat. The change in pressure is attended by a change in the sounds heard through the stethoscope, as shown in FIG. 1. Here A represents the point at which the K-sounds begin to be heard. The value of pressure which prevails at this point is treated as maximum, or systolic, blood pressure. The K-sounds continue to be heard clearly from point A onward and gradually increase in magnitude. At a point B, the K-sounds develop noise that continues until point C, at which the sounds return to noise-free clarity. The clear sounds continue to grow in intensity from this point until point D, where the K-sounds decrease in magnitude. The K-sounds continue losing intensity until point E, at which they vanish. The World Health Organization (WHO) recognizes point D as indicating minimum, or diastolic, blood pressure, while the Japan Insurance Association recognizes point E as indicating diastolic blood pressure.

When measuring blood pressure by auscultation, so-called "stethoscopic gaps" are sometimes encountered due to an occasional pause in the sound of blood flow during measurement. This is construed as being related to such factors as a rise in blood pressure, a decline in blood vessel resistance and the like and frequently occurs between the points B and C in FIG. 1. The phenomenon is seen in 8% of individuals afflicted with hypertension. An example of stethoscopic gaps is illustrated in FIG. 2.

(A) through (F) in FIG. 2 indicate the state of K-sound pick-up by stethoscopy when gradually reducing the pressure applied to a blood vessel. Depressurization begins with (A) and ends with (F), with the attendant change in the K-sounds being as shown. In FIG. 2, (a) through (j) indicate the occurrence of stethoscopic gap.

Noise is dealt with in the conventional blood pressure measuring apparatus in the following manner. When what appears to be a K-sound has been detected, the next K-sound should occur within a predetermined period of time. When it does not, the signal initially detected as the apparent K-sound is treated as noise. The problem encountered with this conventional approach is that if, during the course of measurement, K-sounds become so small as to be longer detectable or a change in the K-sound pattern occurs (or if a pulsating sound ascribable to the patient's pulse is produced), the K-sounds detected up to that time are construed to be noise, even though such is not actually the case. The result is that the point at which systolic blood pressure occurs is detected erroneously.

Some apparatus for blood pressure measurement come equipped with a mechanism for calculating the patient's pulse rate. In an apparatus of this type, pulse rate generally is calculated by converting the K-sound occurrence interval (or the average inverval) into the number of such occurrences per minute. However, there are occasions in the course of measurement where the amplitude of the K-sounds becomes so small as to render the K-sounds undetectable, or where there is a change in the pattern of the K-sounds, so that some K-sounds go undetected. The problem here is that if the K-sound occurrence interval at such time is used in the calculation of pulse rate, an erroneous value of pulse rate, which is lower than the true pulse rate, will be derived.

If a threshold value or pattern for distinguishing the K-sounds were to be so set as to enable diminished K-sounds or the sound of the patient's pulse to be detected in the course of measurement, a pulse sound which is produced before the K-sounds start to appear would be detected as a K-sound or, likewise, a pulse sound which occurs after the K-sounds vanish would detected as a K-sound, thus making it impossible to obtain correct systolic and diastolic blood pressure values.

SUMMARY OF THE INVENTION

The present invention has been devised to solve the aforementioned problems encountered in the prior art.

Accordingly, an object of the present invention is to provide a method and apparatus for measuring circulatory function without measuring the value of systolic blood pressure erroneously because of the "stethoscopic gap" phenomenon mentioned above.

Another object of the present invention is to provide a method and apparatus for measuring circulatory function without measuring the value of diastolic blood pressure erroneously because of the "stethoscopic gap" phenomenon.

Still another object of the present invention is to provide a method and apparatus for measuring circulatory function without measuring pulse rate erroneously because of the "stethoscopic gap" phenomenon.

A further object of the present invention is to provide a method and apparatus for measuring circulatory function without the influence of the "stethoscopic gap" phenomenon.

According to the present invention, the foregoing objects are attained by providing a circulatory function measurement apparatus comprising: pressure control means for controlling pressure applied to a blood vessel of a living body; sound detecting means for detecting a sound from the blood vessel produced due to a change in a value of the pressure applied to the blood vessel by the pressure control means; first recognition means for recognizing whether a sound from the blood vessel detected by the sound detecting means agrees with a first specific condition; second recognition means for recognizing whether a sound from the blood vessel detected by the sound detecting means agrees with a second specific condition less stringent than the first specific condition; and measuring means for measuring circulatory function based on recognition information from the first and second recognition means. The measuring means selectively measures the recognition information from the first recognition means when there is a reduction in the pressure applied to the blood vessel by the pressure control means, selectively measures the recognition information from the second recognition means when the first recognition means recognizes that the sound from the blood vessel agrees with the first specific condition, this latter measurement being made for a predetermined period of time after such recognition, and again selectively measures the recognition information from the first recognition means after said predetermined period of time.

In a preferred embodiment of the present invention, the first recognition means recognizes a K-sound.

In another preferred embodiment of the present invention, the second recognition means recognizes a sound produced by blood flowing through the blood vessel.

The foregoing objects are attained by providing a circulatory function measurement apparatus comprising: pressure control means for controlling pressure applied to a blood vessel of a living body; sound detecting means for detecting a sound from the blood vessel produced due to a change in a value of the pressure applied to the blood vessel by the pressure control means; first recognition means for recognizing whether a sound from the blood vessel detected by the sound detecting means agrees with a first specific condition; second recognition means for recognizing whether a sound from the blood vessel detected by the sound detecting means agrees with a second specific condition less stringent than the first specific condition; and measuring means for measuring circulatory function based on recognition information from the first and second recognition means. When there is a reduction in the pressure applied to the blood vessel by the pressure control means, the measuring means selects the recognition information from the first recognition means and treats as a systolic blood pressure value a blood pressure value which prevails when the first recognition means recognizes an initial sound from the blood vessel that agrees with the first specific condition. Thereafter, the measuring means selects the recognition information from the second recognition means to measure pulse rate and again selects the recognition information from the first recognition means and treats as a diastolic blood pressure value a blood pressure value which prevails when the first recognition means recognizes a final sound from the blood vessel that agrees with the first specific condition.

In a preferred embodiment of the present invention, the first recognition means recognizes a K-sound.

In another preferred embodiment of the present invention, the second recognition means recognizes a sound produced by blood flowing through the blood vessel.

The foregoing objects are attained by providing a circulatory function measurement apparatus comprising: pressure control means for controlling pressure applied to a blood vessel of a living body; sound detecting means for detecting a sound from the blood vessel produced due to a change in a value of the pressure applied to the blood vessel by the pressure control means; first recognition means for recognizing whether a sound from the blood vessel detected by the sound detecting means agrees with a first specific condition; second recognition means for recognizing whether a sound from the blood vessel detected by the sound detecting means agrees with a second specific condition less stringent than the first specific condition; and measuring means for measuring circulatory function based on recognition information from the first and second recognition means. When there is a reduction in the pressure applied to the blood vessel by the pressure control means, the measuring means selects the recognition information from the first recognition means and treats as a systolic blood pressure value a blood pressure value which prevails when the first recognition means recognizes an initial sound from the blood vessel that agrees with the first specific condition. Thereafter, the measuring means selects the recognition information from the second recognition means to judge the correctness of the systolic blood pressure value and again selects the recognition information from the first recognition means and treats as a diastolic blood pressure value a blood pressure value which prevails when the first recognition means recognizes a final sound from the blood vessel that agrees with the first specific condition.

In a preferred embodiment of the present invention, the first recognition means recognizes a K-sound.

In another preferred embodiment of the present invention, the second recognition means recognizes a sound produced by blood flowing through the blood vessel.

The foregoing objects are attained by providing a circulatory function measurement apparatus comprising: pressure control means for controlling pressure applied to a blood vessel of a living body; sound detecting means for detecting a sound from the blood vessel produced due to a change in a value of the pressure applied to the blood vessel by the pressure control means; first recognition means for recognizing whether a sound from the blood vessel detected by the sound detecting means agrees with a first specific condition; second recognition means for recognizing whether a sound from the blood vessel detected by the sound detecting means agrees with a second specific condition less stringent than the first specific condition; and measuring means for measuring circulatory function based on recognition information from the first and second recognition means. When there is a reduction in the pressure applied to the blood vessel by the pressure control means, the measuring means selects the recognition information from the first recognition means and treats as a systolic blood pressure value a blood pressure value which prevails when the first recognition means recognizes an initial sound from the blood vessel that agrees with the first specific condition. Thereafter, the measuring means selects the recognition information from the second recognition means to decide whether the pressure applied to the blood vessel by the pressure control means is deficient or excessive and again selects the recognition information from the first recognition means and treats as a diastolic blood pressure value a blood pressure value which prevails when the first recognition means recognizes a final sound from the blood vessel that agrees with the first specific condition.

In a preferred embodiment of the present invention, the first recognition means recognizes a K-sound.

In another preferred embodiment of the present invention, the second recognition means recognizes a sound produced by blood flowing through the blood vessel.

According to another aspect of the present invention, the foregong objects are attained by providing a circulatory function measurement method comprising steps of: applying pressure to a blood vessel of a living body; reducing the pressure applied to the blood vessel; measuring circulatory function at the beginning of the reduction in pressure based on a sound from the blood vessel that agrees with a first specific condition; measuring circulatory function based on a sound from the blood vessel that agrees with a second specific condition when an initial sound from the blood vessel that agrees with the first specific condition is recognized, the measurement being performed for a predetermined period of time following the recognition of the sound; and measuring circulatory function again based on the sound that agrees with the first specific condition after said predetermined period of time.

In a preferred embodiment of the present invention, the first specific condition is a condition specifying a K-sound.

In another preferred embodiment of the present invention, the second specific condition is a condition specifying a sound produced by blood flowing through the blood vessel.

Further, the objects of the present invention are attained by providing a circulatory function measurement method comprising steps of: applying pressure to a blood vessel of a living body; reducing the pressure applied to the blood vessel; treating as a systolic blood pressure value a blood pressure value which prevails when an initial sound from the blood vessel that agrees with a first specific condition is recognized as the pressure is being reduced; measuring pulse rate based on an inital sound from the blood vessel that agrees with the first specific condition or a sound from the blood vessel that agrees with a second specific condition less stringent than the first specific condition; and treating as a diastolic blood pressure value a blood pressure value which prevails when a final sound from the blood vessel that agrees with the first specific condition is recognized.

In a preferred embodiment of the present invention, the first specific condition is a condition specifying a K-sound.

In another preferred embodiment of the present invention, the second specific condition is a condition specifying a sound produced by blood flowing through the blood vessel.

Further, the objects of the present invention are attained by providing a circulatory function measurement method comprising steps of: applying pressure to a blood vessel of a living body; reducing the pressure applied to the blood vessel; treating as a systolic blood pressure value a blood pressure value which prevails when an initial sound from the blood vessel that agrees with a first specific condition is recognized as the pressure is being reduced; judging the correctness of the systolic blood pressure value based on an initial sound from the blood vessel that agrees with the first specific condition or a sound from the blood vessel that agrees with a second specific condition less stringent than the first specific condition; and treating as a diastolic blood pressure value a blood pressure value which prevails when a final sound from the blood vessel that agrees with the first specific condition is recognized.

In a preferred embodiment of the present invention, the first specific condition is a condition specifying a K-sound.

In another preferred embodiment of the present invention, the second specific condition is a condition specifying a sound produced by blood flowing through the blood vessel.

Further, the objects of the present invention are attained by providing a circulatory function measurement method comprising steps of: applying pressure to a blood vessel of a living body; reducing the pressure applied to the blood vessel; treating as a systolic blood pressure value a blood pressure value which prevails when an initial sound from the blood vessel that agrees with a first specific condition is recognized as the pressure is being reduced; deciding whether the pressure applied to the blood vessel is deficient or excessive based an initial sound from the blood vessel that agrees with the first specific condition or a sound from the blood vessel that agrees with a second specific condition less stringent than the first specific condition; and treating as a diastolic blood pressure value a blood pressure value which prevails when a final sound from the blood vessel that agrees with the first specific condition is recognized.

In a preferred embodiment of the present invention, the first specific condition is a condition specifying a K-sound.

In another preferred embodiment of the present invention, the second specific condition is a condition specifying a sound produced by blood flowing through the blood vessel.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 7(A), (B) are flowcharts illustrating processing for recognition of sounds that agree with specific conditions according to an embodiment of the present invention.

DESCRIPTION OF THE PREFERRED EMBODIMENT

An embodiment of the present invention will now be described in detail with reference to the accompanying drawings.

Figure 3:
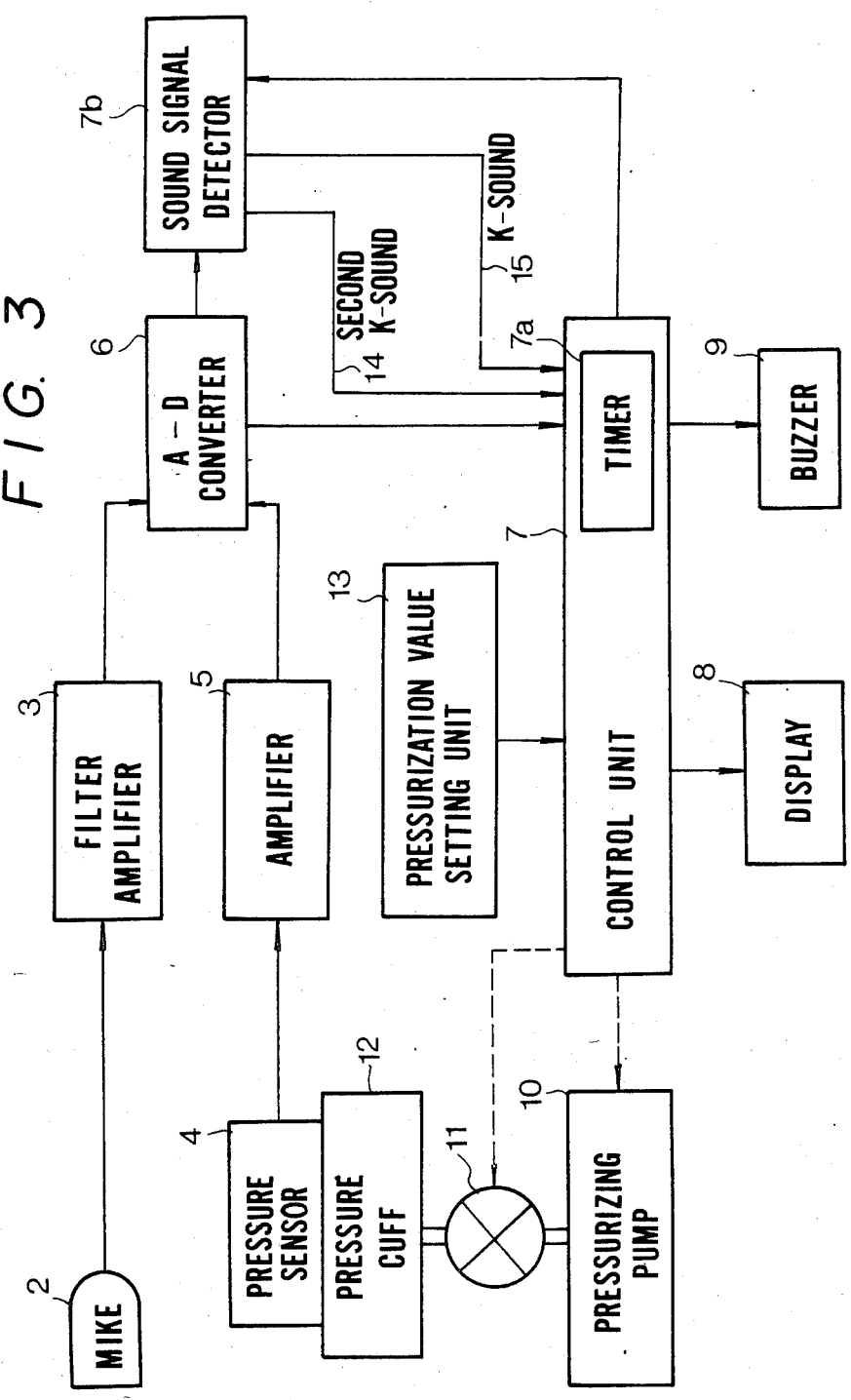
FIG. 3 is a block diagram illustrating an embodiment of the present invention.

FIG. 3 illustrates an embodiment of a circulatory function measurement apparatus according to the present invention. The apparatus includes a microphone 2 attached to the lower edge of a pressure cuff 12 so that the microphone will be positioned near the bend in a patient's forearm opposite the elbow when the the cuff 12 is affixed to the upper portion of the patient's arm. The microphone 2 is adapted to detect sounds, which are emitted from the patient's blood vessel, that agree with specific conditions, described below, and to produce an output signal indicative thereof. The abovementioned sound produced by the blood vessel shall be referred to as a "blood vessel sound" hereafter. The output signal from the microphone 2 is applied to a filter amplifier 3 for selecting and amplifying a required frequency component of the signal indicative of the blood vessel sound that agrees with the specific conditions. Also attached to the pressure cuff 12 is a pressure sensor 4 for sensing pressure and for producing an output signal indicative of the pressured sensed. This signal is amplified by an amplifier 5. The outputs of the filter amplifier 3 and amplifier 5, both of which are analog signals, are applied to an A-D converter 6 which converts these signals into digital signals. The digital output of the A-D converter 6 is inputted to a control unit 7. The latter detects a K-sound from the signal indicative of the blood vessel sound from microphone 2 that agrees with the specific conditions, detects the pressure of cuff 12 that prevails when the K-sound is detected, executes blood pressure measurement processing on the basis of the detected K-sound and detected pressure, and causes a display 8 to display the results of such processing, such as systolic and diastolic blood pressure. The control unit 7 incorporates a timer circuit 7a and is connected to a blood vessel sound signal detector 7b which detects a blood vessel sound signal that agrees with the specific conditions. The detector 7b, the function of which will be described later, receives the output of the microphone following its amplification and conversion into a digital signal and has output lines 14, 15 connected to the control unit 7. An output on line 14 indicates that a second K-sound in a series thereof has been detected, and an output on line 15 indicates merely that a K-sound has been detected. The control unit 7, timer circuit 7a and detector 7b preferably are constructed in the form of a one-chip microprocessor. The control unit 7 is also connected to a buzzer 9. A pressurizing pump 10 is connected to the pressure cuff 12 through a discharge valve 11 which, under the control of the control unit 7, is capable of venting the air from the cuff 12 to gradually reduce its pressure. Also connected to the control unit 7 is a setting unit 13 for setting the pump 10 to a cuff pressurization value through the intermediary of the control unit 7.

Figure 4:
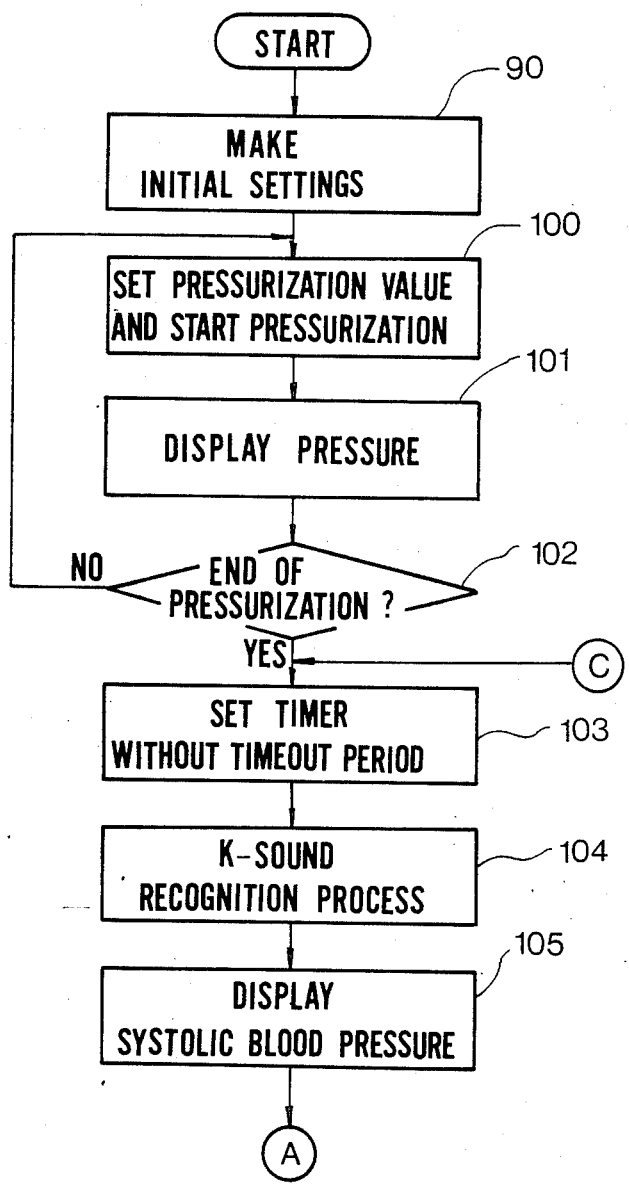
FIG. 4 is a flowchart illustrating control of measurement for determining systolic blood pressure, diastolic blood pressure and pulse rate according to an embodiment of the present invention.
Figure 4:
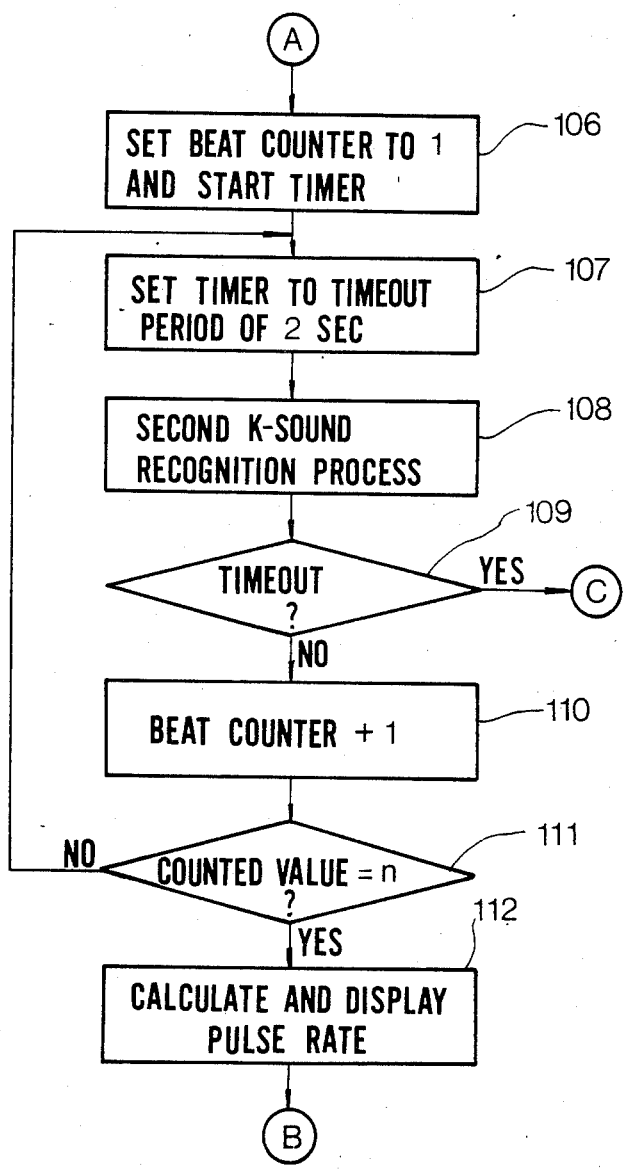

Reference will now be had to the flowchart of FIG. 4 to describe processing for recognizing a blood vessel sound that agrees with specific conditions. The apparatus of FIG. 3, particularly the control unit 7, is used for executing this processing.

When power is introduced at the control unit 7, the power supply is subjected to a battery check and such initial settings as a pressure zeroing adjustment are made at a step S90. At the end of the initial settings, the preparations for blood pressure measurement are completed and the system enters a stand-by mode to await the start of measurement. When blood pressure measurement commences, the program moves to a step S100, which calls for the pressurization setting unit 13 to be set to a pressurization value. This is accomplished by pressing a pressurization switch, which is not shown. When the pressurization switch is pressed, the control unit 7 actuates the pressurization pump 10, which responds by pressurizing the cuff 12. Next, at a step S101, the control unit 7 causes the display 8 to display the value of pressure applied to the patient's blood vessel by the pressurized cuff 12. The applied pressure is sensed approximately every 0.5 sec by the pressure sensor 4, the analog output whereof is converted into a digital signal by the A-D converter 6 for application to the control unit 7. Thus, the digital pressure signal is applied to the control unit 7 approximately every 0.5 sec. The control unit 7 compares the pressure signal currently being received with the last pressure signal inputted thereto and renders a decision to the effect that pressurization has taken place when the currently arriving pressure signal indicates a pressure increase of 5 mmHg or more over the last signal. This is to deal with an arrangement in which the pressurization pump 10 is a manually operated pump such as a rubber pressure bulb for performing pressurization by hand.

Next, decision step S102 calls for monitoring to determine whether pressurization has ended. If pressurization ends, the next step executed is a step 103; if not, the program returns to the step S101. Thus, pressure values are displayed in successive fashion. It should be noted that the end of pressurization is indicated when equivalence is established between the value set by the setting unit 13 and the measured value of pressure, or when there is absolutely no increase in pressure over a period of 1 sec.

Step S103 executed at the end of pressurization calls for setting of the timer circuit 7a to zero without a timeout period. Next, at a step S104, a K-sound recognition subroutine, described below, is called. Processing returns to the main routine from this subroutine when a time set in timer circuit 7a expires or when a decision is rendered to the effect that a K-sound has been recognized. Accordingly, the program will proceed from step S104 to step S105 only when the timer circuit 7a is set without a timeout period being imposed on it and a K-sound is recognized. Therefore, since the pressure in cuff 12 at the detection of this K-sound will be indicative of the patient's systolic blood pressure, the prevailing pressure is recognized as the systolic blood pressure and the pressure reading on the display unit 8 is frozen to present a display of the systolic blood pressure value. This is step S105 of the flowchart.

This is followed by a step S106, at which a beat counter (not shown) in the control unit 7 is set to 1, the timer circuit 7a is reset to zero and the clocking of time from this moment onward is started.

Next, at a step S107, the timer circuit 7a is set to a timeout period of two seconds. The timer circuit 7a, the timeout period of which has been set, is adapted to set a timeout flag regardless of the clocked time when a predetermined time period to which it has been set expires, and thereafter resets the timeout flag in response to resetting of the timeout period.

A second K-sound recognition subroutine, described below, is called at a step S108. In comparison with the K-sound recognition subroutine, the second K-sound recognition subroutine lowers a threshold value used for K-sound recognition and widens the range of a K-sound recognition pattern to make possible the recognition not only of the K-sounds but also of the sound of the blood vessel pulse, i.e., the aforementioned blood vessel sounds. The processing of this subroutine also ends and a return to the main routine is effected when a timeout flag is set or when a K-sound is recognized. Consequently, it is checked at a step S109 whether a timeout has occurred, i.e., whether a K-sound has not been recognized, in the abovementioned set period of two seconds. If a K-sound is not recognized in the period of two seconds, this means that the earlier recognized K-sound was noise. As a result, the program returns to the step S103. If there is no timeout at step S109, the program proceeds to a step S110, at which the beat counter is incremented by one step. It is then determined at a step S111 whether the status of the beat counter is a predetermined value n; if it is not, then the program returns to the step S107 and processing for detecting the next K-sound is executed. If the value in the beat counter attains the value n, then the program proceeds to a step S112. In the present embodiment, the predetermined value n is seven.

The step S112 is for calculating the number of beats of the patient's pulse per minute from (a) the time clocked by timer circuit 7a, which started measuring time at the step S106, and (b) the value in the beat counter, and for displaying the calculated value in a pulse rate display section of the display unit 8.

Figure 2:
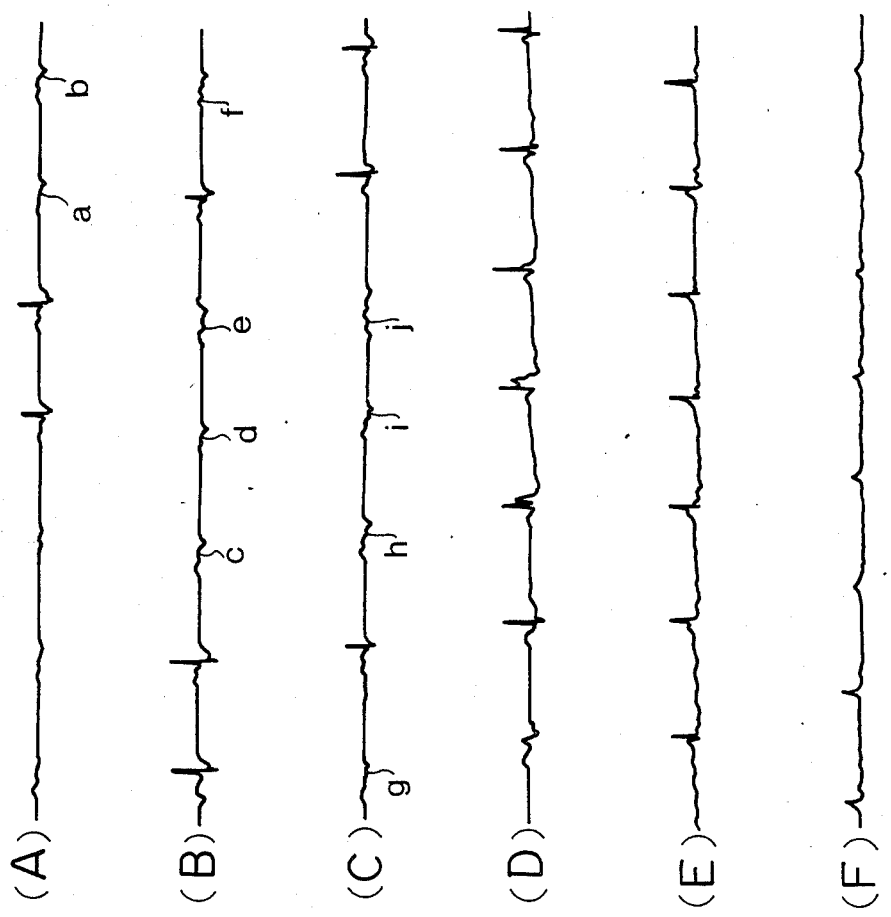
FIG. 2 is a waveform diagram illustrating detected K-sounds in a case where stethoscopic gaps occur.
Figure 1:
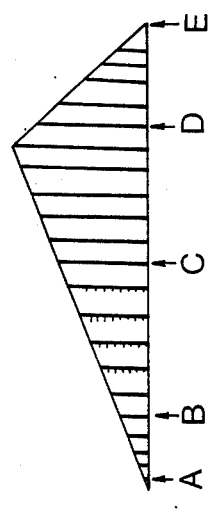
FIG. 1 is a view illustrating the manner in which a K-sound appears through auscultation.

In the foregoing processing, measurement of pulse rate is performed after it is recognized that the first beat of the blood vessel sound satisfies the requirements of a K-sound. In other words, measurement of pulse rate is performed after the first K-sound is recognized, namely after recognition of systolic blood pressure. However, there is no difficulty even if the stethoscopic gaps (a–j in FIG. 2) should happen to be encountered between B and C in FIG. 1. More specifically, since processing changes over from ordinary K-sound recognition to second K-sound recognition processing, the second K-sound recognition processing enables the sound of the patient's pulse to be detected so that these sounds can be used for pulse rate measurement in place of the K-sounds. Therefore, even if K-sounds become intermittent between B and C in FIG. 1 owing to the stethoscopic gap phenomenon, erroneous recognition of both systolic blood pressure and pulse rate can be prevented.

Following the step S112, the program proceeds to the steps for detecting diastolic blood pressure. Note that if a threshold value or pattern for discriminating K-sounds is so set as to enable the detection also of K-sounds which become small in amplitude in the course of measurement, then even the sounds of the patient's pulse that occur after the extinction of the K-sounds are detected as the K-sounds and a correct blood pressure value is no longer obtained. Therefore, after the pulse rate, in terms of beats per minute, is displayed at the step S112, a timeout period of 4.5 seconds for detection of diastolic blood pressure is set in the timer circuit 7a, after which the K-sound recognition subroutine is called at a step S114.

When the program returns from the K-sound recognition subroutine of step S114, a K-sound will have been detected or the timeout period of 4.5 seconds will have elapsed. Therefore, the next step S115 is to determine whether the time of 4.5 seconds has run out. If the answer is negative, i.e., if a K-sound has been recognized, the program proceeds to a step S116, where the value of pressure prevailing at K-sound recognition and sensed by the pressure sensor 4 is stored in a pressure register (not shown) in the control unit 7, after which the program returns to the step S113. Here the timeout of 4.5 seconds is set again and the next K-sound is awaited.

If timeout is confirmed at the step S115, this indicates that a K-sound has not been detected. As a result, the program proceeds to a step S117, where the value in the pressure register, namely the value of the pressure in cuff 12 that prevailed when a K-sound was last recognized, is displayed as diastolic blood pressure in a corresponding display section of the display unit 8. This ends the processing for measurement of both blood pressure and pulse rate.

Note that the timeout period of 4.5 seconds is adopted in order to take stethoscopic gaps into account. Since stethoscopic gaps generally occur for one or two or, at most, three consecutive beats, diastolic blood pressure is construed to have been detected when K-sounds are not detected over the period of 4.5 seconds.

Let us now describe the processing for the K-sound recognition subroutine and second K-sound recognition subroutine.

Figure 5:
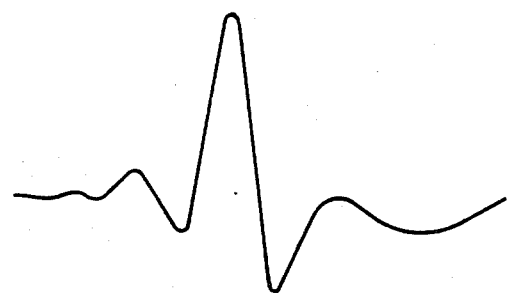
FIGS. 5 and 6 are views illustrating a K-sound waveform.
Figure 6:
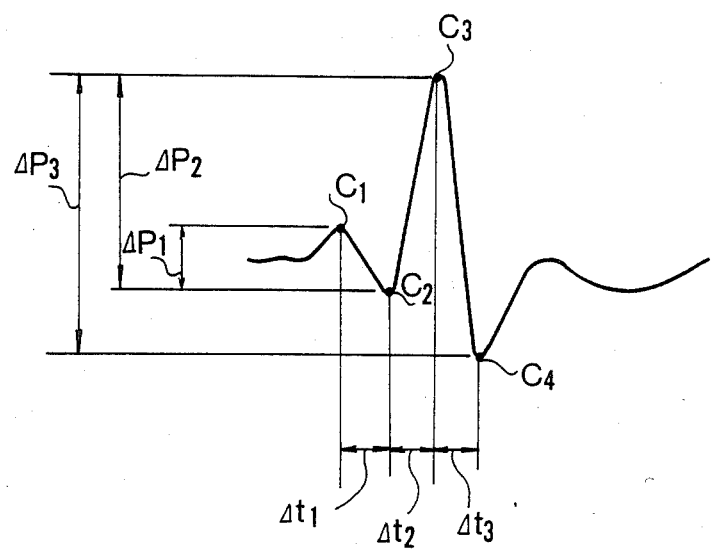

A common K-sound waveform picked up by auscultation is as shown in FIG. 5. In an embodiment of the present invention, this K-sound waveform is subjected to pattern recognition. The method of pattern recognition includes detecting four characterizing points C1–C4 on the waveform, as shown in FIG. 6, and determining whether a waveform is indeed a K-sound waveform based on the positional relationship of these points. For example, to judge whether the positional relationship between points C1, C2 satisfies the condition for a K-sound, it is determined whether a crest difference $\Delta P_1$ and a time difference $\Delta t_1$ between C1 and C2 fall within respective stipulated limits. Conditions are set in like fashion with respect to the other characterizing points as well. A similar practice is followed also for a plurality of waveform patterns.

With this as a background, we will now describe processing for the K-sound recognition subroutine with reference to FIG. 7(A).

When the K-sound recognition subroutine is called, the first step S700 calls a subroutine for detecting the characterizing points C1–C4 to initiate processing for detection of these points. Though the subroutine for detecting C1–C4 is represented here solely as the step S700 for convenience of description, the aforementioned detector 7b, which detects the signal indicative of sounds that agree with the specific conditions, preferably reads in sound data from the microphone 2 (via the filter amplifier 3 and A-D converter 6) constantly at predetermined time intervals and detects points of maxima and minima indicated hereinbelow. Signals indicative of a K-sound in general and of a second K-sound are inputted to the control unit 7 over signal lines 15, 14, respectively.

In the C1–C4 detection subroutine, data indicative of sounds which exceed a threshold value are obtained. In the subroutine, the level of such sound data which appeared at the previous instant of read-in and the level of sound data prevailing at the current instant of read-in are compared. When the difference between them indicates a transition from an increasing tendency to a decreasing tendency, the sound data (maximum point) prevailing at such time is written into a memory (not shown) in the control unit 7. When the difference between the two compared levels indicates a transition from a decreasing tendency to an increasing tendency, the sound data (minimum point) prevailing at such time is written into the memory. Concurrently, the instants in time at which these points are detected are also written into memory. Thus, detected points of maxima and minima and the times at which these points are detected are written into memory in successive fashion. All of these steps correspond to the subroutine of step S700.

Next, at a step S701, it is determined whether the timeout flag of timer circuit 7a has been set. If the flag has been set, the program returns to the main routine; if not, the program proceeds to a step S702 and processing in accordance with a K-sound decision algorithm is executed. It is thus determined, in accordance with the following algorithm serving as one example, whether the characterizing points C1–C4 fall within the respective predetermined limits of the pattern.

"K-SOUND DECISION" ALGORITHM
```
if A1 < ΔP1 < B1 & C1 < Δt1 < D1
then if A2 < ΔP2 < B2 & C2 < Δt2 < D2
then if A3 < ΔP3 < B3 & C3 < Δt3 < D3
then if —
then "waveform is K-sound waveform"
else "waveform is not K-sound waveform"
fi
fi
fi
return
```

When a K-sound is recognized at the next step S703, the program returns to the main routine. If no K-sound is recognized at step S703, then processing for K-sound recognition is reexecuted starting from the step S700.

According to the second K-sound recognition subroutine as shown in FIG. 7(B), C1–C4 detection processing, similar to that of step S700 in FIG. 7(A), is executed at a step S710. Next, at a step S711, it is determined whether the timeout flag of timer circuit 7a has been set. If the flag has been set, the program returns to the main routine; if not, processing in accordance with a second K-sound decision algorithm is executed. It is thus determined, in accordance with the following algorithm serving as one example, whether the characterizing points C1–C4 fall within the respective predetermined limits of the pattern.

"SECOND K-SOUND DECISION" ALGORITHM
```
if A1−a1 < ΔP1 < B1+b1 & C1−c1 < Δt1 < D1+d1
then if A2−a2 < ΔP2 < B2+b2 & C2−c2 < Δt2 < D2+d2
then if A3−a3 < ΔP3 < B3+b3 & C3−c3 < Δt3 < D3+d3
then if —
then "waveform is K-sound waveform"
else "waveform is not K-sound waveform"
fi
fi
fi
return
```

In the above, ai, bi, ci (i=1, 2, 3) are positive. In addition, the conditions contained in the "K-sound decision" are excluded in the "second K-sound decision" as the case demands.

The next step is a step S713, where it is determined whether there is agreement with the second K-sound pattern; if there is not, the program returns to the step S710 to continue the second K-sound recognition processing.

According to the embodiment described above, K-sound recognition and second K-sound recognition can be switched between merely by converting parameters so that the processing program can be kept short in length.

Further, with the circulatory function measurement apparatus of the present invention as set forth above, the first beat of a K-sound can be detected without fail. In addition, by relaxing the K-sound recognition requirement for a predetermined period of time following K-sound detection, circulatory function can be measured reliably and accurately even if stethoscopic gaps occur.

In accordance with the present invention, the first beat of a K-sound is recognized in accordance with the strict, ideal conditions and the conditions for recognition of the K-sounds are relaxed over the period in which stethoscopic gaps occur. This enables inadequate pressurization to be judged accurately and assures that a first beat of a K-sound will no longer be erroneously detected and judged to be K-sound because of noise when such is not the case. As a result, the correct value of systolic blood pressure can be detected and the correct value of pulse rate can be measured. Moreover, since K-sounds are again recognized in accordance with the stricter ideal conditions when detecting diastolic blood pressure, the latter can be measured without error.

Further, the circulatory function measurement method provided by the present invention includes executing recognition processing in accordance with strict, ideal conditions when the first beat of a K-sound is to be recognized for detecting systolic blood pressure, relaxing the K-sound recognition conditions when stethoscopic gaps occur after recognition of the first beat of a K-sound, measuring the correct systolic blood pressure and pulse rate by accurately detecting K-sounds and the beats of the patient's pulse, and thereafter performing K-sound recognition again in accordance with the stricter ideal conditions when a final K-sound is to be recognized at cuff depressurization for the purpose of measuring diastolic blood pressure. This method enables circulatory function to be measured with highly accurate results.

In the illustrated embodiment, the measurement of pulse rate begins with the occurrence of the first K-sound. However, a circulatory function measurement apparatus of even greater reliability can be obtained if measurement of pulse rate is started when the stethoscopic gaps become small in amplitude a prescribed period of time after the first K-sound.

As many apparently widely different embodiments of the present invention can be made without departing from the spirit and scope thereof, it is to be understood that the invention is not limited to the specific embodiments thereof except as defined in the appended claims.

What is claimed is:

1. A circulatory function measurement apparatus comprising:
   pressure control means for controlling pressure applied to a blood vessel of a living body;
   sound detecting means for detecting a sound from the blood vessel produced due to a change in a value of the pressure applied to the blood vessel by said pressure control means;
   first recognition means for recognizing whether the sound from the blood vessel detected by said sound detecting means agrees with a first specific condition and for generating first recognition information indicating agreement with the first specific condition;
   second recognition means for recognizing whether a sound from the blood vessel detected by said sound detecting means agrees with a second specific condition less stringent than the first specific condition and for generating second recognition information indicating agreement with the second specific condition; and
   measuring means for measuring first and second parameters of circulatory function based on the first and second recognition information from said first and second recognition means, said measuring means selectively measuring the first parameter of circulatory function based upon the first recognition information from said first recognition means when there is a reduction in the pressure applied to the blood vessel by said pressure control means, said measuring, means selectively measuring the second parameter of circulator function based upon the second recognition information from said second recognition means when said first recognition means recognizes that the sound from the blood vessel agrees with the first specific condition, this latter measurement being made for a predetermined period of time after such recognition, and said measuring means again selectively measuring the first parameter of circulatory function based upon the first recognition information from said first recognition means after the predetermined period of time.

2. The apparatus according to claim 1, wherein said first recognition means recognizes a Korotkoff sound.

3. The apparatus according to claim 1, wherein said second recognition means recognizes a sound produced by blood flowing through the blood vessel.

4. A circulatory function measurement apparatus comprising:
   pressure control means for controlling pressure applied to a blood vessel of a living body;
   sound detecting means for detecting a sound from the blood vessel produced due to a change in a value of the pressure applied to the blood vessel by said pressure control means;
   first recognition means for recognizing whether a sound from the blood vessel detected by said sound detecting means agrees with a first specific condition;
   second recognition means for recognizing whether a sound from the blood vessel detected by said sound detecting means agrees with a second specific condition less stringent than the first specific condition; and
   measuring means for measuring circulatory function based on recognition information from said first and second recognition means;
   wherein when there is on the decrease in the pressure applied to the blood vessel by said pressure control means, said measuring means selects the recognition information from said first recognition means and treats as a systolic blood pressure value a blood pressure value which prevails when said first recognition means recognizes an initial sound from the blood vessel that agrees with the first specific condition, and thereafter selects the recognition information from said second recognition means to measure pulse rate and again selects the recognition information from said first recognition means and treats as a diastolic blood pressure value a blood pressure value which prevails when said first recognition means recognizes a final sound from the blood vessel that agrees with the first specific condition.

5. The apparatus according to claim 4, wherein said first recognition means recognizes a Korotkoff sound.

6. The apparatus according to claim 4, wherein said second recognition means recognizes a sound produced by blood flowing through the blood vessel.

7. A circulatory function measurement apparatus comprising:
   pressure control means for controlling pressure applied to a blood vessel of a living body;
   sound detecting means for detecting a sound from the blood vessel produced due to a change in a value of the pressure applied to the blood vessel by said pressure control means;
   first recognition means for recognizing whether a sound from the blood vessel detected by said sound detecting means agrees with a first specific condition;
   second recognition means for recognizing whether a sound from the blood vessel detected by said sound detecting means agrees with a second specific condition less stringent than the first specific condition; and
   measuring means for measuring circulatory function based on recognition information from said first and second recognition means;
   wherein when there is a reduction in the pressure applied to the blood vessel by said pressure control means, said measuring means selects the recognition information from said first recognition means and treats as a systolic blood pressure value a blood pressure value which prevails when said first recognition means recognizes an initial sound from the blood vessel that agrees with the first specific condition, and thereafter selects the recognition information from said second recognition means to judge the correctness of the systolic blood pressure value and again selects the recognition information from said first recognition means and treats as a diastolic blood pressure value a blood pressure value which prevails when said first recognition means recognizes a final sound from the blood vessel that agrees with the first specific condition.

8. The apparatus according to claim 7, wherein said first recognition means recognizes a Korotkoff sound.

9. The apparatus according to claim 7, wherein said second recognition means recognizes a sound produced by blood flowing through the blood vessel.

10. A circulatory function measurement apparatus comprising:
    pressure control means for controlling pressure applied to a blood vessel of a living body;
    sound detecting means for detecting a sound from the blood vessel produced due to a change in a value of the pressure applied to the blood vessel by said pressure control means;
    first recognition means for recognizing whether a sound from the blood vessel detected by said sound detecting means agrees with a first specific condition;
    second recognition means for recognizing whether a sound from the blood vessel detected by said sound detecting means agrees with a second specific condition less stringent than the first specific condition; and
    measuring means for measuring blood pressure and pulse rate based on recognition information from said first and second recognition means;
    wherein when there is a reduction in the pressure applied to the blood vessel by said pressure control means, said measuring means selects the recognition information from said first recognition means and treats as a systolic blood pressure value a blood pressure value which prevails when said first recognition means recognizes an initial sound from the blood vessel that agrees with the first specific condition, and thereafter selects the recognition information from said second recognition means to decide whether the pressure applied to the blood vessel by the pressure control means is adequate and again selects the recognition information from said first recognition means and treats as a diastolic blood pressure value a blood pressure value which prevails when said first recognition means recognizes a final sound from the blood vessel that agrees with the first specific condition.

11. The apparatus according to claim 10, wherein said first recognition means recognizes a Korotkoff sound.

12. The apparatus according to claim 10, wherein said second recognition means recognizes a sound produced by blood flowing through the blood vessel.

13. A circulatory function measurement method comprising steps of:
applying pressure to a blood vessel of a living body;
reducing the pressure applied to the blood vessel;
measuring circulatory function at the beginning of the reduction in pressure based on a sound from the blood vessel that agrees with a first specific condition;
measuring circulatory function based on a sound from the blood vessel that agrees with a second specific condition when an initial sound from the blood vessel that agrees with the first specific condition is recognized, the measurement being performed for a predetermined period of time following the recognition of the sound; and
measuring circulatory function again based on the sound that agrees with the first specific condition after said predetermined period of time.

14. The method according to claim 13, wherein the first specific condition is a condition specifying a Korotkoff sound.

15. The method according to claim 13, wherein the sound specific condition is a condition specifying a sound produced by blood flowing through the blood vessel.

16. A circulatory function measurement method comprising of:
applying pressure to a blood vessel of a living body;
reducing the pressure applied to the blood vessel;
measuring a systolic blood pressure based on a a sound from the blood vessel that agrees with a first specific condition, as the pressure is being reduced;
measuring pulse rate based on sounds from the blood vessel that agree with a second specific condition less stringent than the first specific condition for a predetermined period of time following recognition of an initial sound from the blood vessel that agrees with the first specific condition; and
measuring diastolic blood pressure based on a sound from the blood vessel that agrees with the first specific condition after the predetermined period of time.

17. The method accroding to claim: 16, wherein the first specific condition is a condition specifying a Korotkoff sound.

18. The method according to claim 16, wherein the second specific condition is a condition specifying a sound produced by blood flowing through the blood vessel.

19. A circulatory function measurement method comprising steps of:
applying pressure to a blood vessel of a living body;
reducing the pressure applied to the blood vessel;
measuring systolic blood pressure based on a sound from the blood vessel that agrees with a first specific condition, as the pressure is being reduced;
judging correctness of the systolic blood pressure based on sounds from the blood vessel that agree with a second specific condition less stringent than the first specific condition for a predetermined period of time following recognition of an initial sound from the blood vessel that agrees with the first specific condition; and
measuring diastolic blood pressure based on a sound from the blood vessel that agrees with the first specific condition after the predetermined period of time.

20. The method according to claim 19, wherein the first specific condition is a condition specifying a Korotkoff sound.

21. The method according to claim 19, wherein the second specific condition is a condition specifying a sound produced by blood flowing through the blood vessel.

22. A circulatory function measurement method comprising steps of:
applying pressure to a blood vessel of a living body;
reducing the pressure applied to the blood vessel;
mesuring systolic blood pressure based on a sound from the blood vessel that agrees with a first specific condition, as the pressure is being reduced;
deciding whether the pressure applied to the blood vessel is adequate based on sounds from the blood vessel that agree with a second specific condition less stringent than the first specific condition for a predetermined period of time following recognition of an initial sound from the blood vessel that agrees with the first specific condition; and
measuring diastolic blood pressure based on a sound from the blood vessel that agrees with the first specific condition after the predetermined period of time.

23. The method according to claim 22, wherein the first specific condition is a condition specifying a Korotkoff sound.

24. The method according to claim 22, wherein the second specific condition is a condition specifying a sound produced by blood flowing through the blood vessel.

* * * * *